(12) United States Patent
Moon

(10) Patent No.: US 8,097,223 B2
(45) Date of Patent: Jan. 17, 2012

(54) AUTOCLAVE WASTE FLUID DISPOSAL DEVICE

(76) Inventor: Lance Moon, Sturgis, SD (US)

( * ) Notice: Subject to any disclaimer, the term of this patent is extended or adjusted under 35 U.S.C. 154(b) by 417 days.

(21) Appl. No.: 12/489,228

(22) Filed: Jun. 22, 2009

(65) Prior Publication Data

US 2010/0322830 A1    Dec. 23, 2010

(51) Int. Cl.
*F28B 5/00* (2006.01)
*A61L 2/00* (2006.01)

(52) U.S. Cl. .................... 422/531; 422/292; 165/302

(58) Field of Classification Search ............. 422/292, 422/531; 165/302; 432/66
See application file for complete search history.

(56) References Cited

U.S. PATENT DOCUMENTS 2,207,838 A * 7/1940 Thomas .................. 62/101
2,441,730 A * 5/1948 Strumia .................. 34/295
3,681,008 A * 8/1972 Black ...................... 422/117

* cited by examiner

*Primary Examiner* — Sean E Conley
(74) *Attorney, Agent, or Firm* — Gordon & Rees LLP

(57) ABSTRACT

An autoclave waste fluid disposal device includes an outer housing container with a main inlet port for receiving waste fluids from an autoclave, and a main outlet port. A multi-chambered condenser inside the outer housing container includes an inlet tube connected to an innermost primary chamber. A secondary chamber envelopes the primary chamber and has an upper end sealed about the inlet tube and at least one secondary chamber outlet port. A tertiary chamber enveloping the secondary chamber has a closed lower end, an upper end sealed about the inlet tube, and at least one tertiary chamber outlet port in communication with the outer housing container. A coil tube encircles the multi-chambered condenser and has a first end connected to the main inlet port of the outer housing container and a second end connected to the inlet tube of the multi-chambered condenser.

18 Claims, 3 Drawing Sheets

AUTOCLAVE WASTE FLUID DISPOSAL DEVICE

FIELD OF THE INVENTION

The present invention relates generally to autoclaves for the sterilization of dental medical and other instruments, and more particularly to a device for preventing such autoclaves from contaminating the surrounding environment.

BACKGROUND OF THE INVENTION

Many dental and medical procedures require the use of relatively expensive specialty equipment, instruments, implements, tools or supplies (hereinafter collectively referred to as "medical equipment" or simply "equipment"). Further, medical equipment must be clean and sterile in order to prevent patients from becoming infected by bacteria, viruses or other infectious agents. Relatively inexpensive medical equipment can be purchased new for each patient and disposed of after use so that there is no need to clean the equipment at all. However, this is simply not economical for expensive medical equipment that may cost hundreds or even thousands of dollars. Instead, such non-disposable medical equipment must be cleaned and sterilized after each use.

One common method for sterilizing medical equipment is the use of an autoclave. An autoclave is a device which sterilizes medical equipment with high temperature (and often high pressure) steam. In some autoclaves, used medical equipment is placed directly inside a steam chamber in the autoclave. Other autoclaves have a removable sealed cassette which is filled with used medical equipment and then inserted into the autoclave where steam is injected inside. Regardless of the specific type of autoclave used, sanitization is achieved by generating steam which is passed over the medical equipment. Many autoclaves are computer controlled so that the sanitization chamber or cassette is held at a particular temperature and pressure for several minutes to ensure that all infectious agents are destroyed. After the process is complete, the medical equipment is clean and sanitary and ready for use on the next patient.

However, although the medical equipment itself is sanitized, the same cannot be said for the environment surrounding the autoclave, which is often the medical or dental office where patients receive care. This is because the autoclave ejects waste steam and air into a waste container or sometimes simply into a sink. Once the steam has reached a sufficiently high temperature to kill any infectious agents, the waste steam and air are sanitized. However, when the steam is first injected into the chamber or cassette, it may not yet be at necessary sanitization temperatures. Further, even if the initial steam injected into the chamber or cassette is adequately heated, the chamber/cassette and equipment are initially at room temperature. When the steam first contacts the relatively cool chamber/cassette and medical equipment, the temperature of the steam is lowered, possibly below necessary sanitization temperatures.

Thus, the waste steam and air initially ejected from the autoclave is not sanitary, at least until the steam exiting the autoclave is above sanitization temperature. This steam and air may harbor infectious agents which are carried around the surrounding environment on air currents, thus potentially contaminating the entire room. Even if the autoclave ejects waste steam and air through a tube into a waste container, the steam and air will escape through leaks into the ambient air. Further, even if the waste steam is sanitary, the warm moist air it creates serves as perfect environment for mold growth in the surrounding area. Accordingly, even though the medical equipment is sanitized by the autoclave, the sanitization process exposes the surrounding environment to trace amounts of potentially dangerous infectious agents.

SUMMARY OF THE INVENTION

The present invention improves upon existing autoclaves and medical equipment sanitation procedures by ensuring that waste steam and heat does not contaminate the environment surrounding the autoclave and is disposed of safely.

In one embodiment, an autoclave waste fluid disposal device includes an outer housing container with a closed lower end, a main inlet port for receiving waste fluids from an autoclave, and a main outlet port. A multi-chambered condenser is mounted inside the outer housing container and includes an inlet tube, an innermost primary chamber having an open lower end and a sealed upper end with an inlet port connected to the inlet tube. The multi-chambered condenser also includes a secondary chamber enveloping the primary chamber and in communication with the open lower end of the primary chamber. The secondary chamber has an upper end sealed about the inlet tube and at least one secondary chamber outlet port. The multi-chambered condenser also includes a tertiary chamber enveloping the secondary chamber. The tertiary chamber has a closed lower end, an upper end sealed about the inlet tube, and at least one tertiary chamber outlet port in communication with the outer housing container. A coil tube encircles the multi-chambered condenser and has a first end connected to the main inlet port of the outer housing container and a second end connected to the inlet tube of the multi-chambered condenser.

The autoclave waste fluid disposal device may further include a drip tube connected to the at least one secondary chamber outlet port and extending toward the lower end of the tertiary chamber. Further, there may also be a second secondary chamber outlet port and a second drip tube connected to the second secondary chamber outlet port and extending toward the lower end of the tertiary chamber.

The main inlet port may be adjacent to the upper end of the outer housing container. The coil tube may include a first segment connected to the main inlet port and extending to the lower end of the outer housing container, and a second segment extending from the lower end of the outer housing container to the upper end of the multi-chambered condenser. The second segment of the coil tube may include a plurality of coils encircling the multi-chambered condenser.

When in use with an autoclave, waste fluid from an autoclave enters the main inlet port of the outer housing container, travels through the coil tube into the inlet tube of the multi-chambered condenser and passes through the inlet port of the primary chamber. The waste fluid expands in the primary chamber and travels out the open lower end of the primary chamber into the lower end of the secondary chamber, then rises inside the secondary chamber and exits the secondary chamber outlet port into the tertiary chamber. The waste fluid then exits the tertiary chamber into the outer housing container, finally exiting the autoclave waste fluid disposal device through the main outlet port of the outer housing container. The waste fluid is thus condensed and cooled in the autoclave waste fluid disposal device such that liquid water exits the autoclave waste fluid disposal device.

In some embodiments the main outlet port of the outer housing container is connected to an exit pipe which is directly connected to a drain pipe in communication with a sewer system.

The outer housing container may be aluminum, and any or all of the primary chamber, the secondary chamber, and the tertiary chamber may be copper. The secondary chamber and tertiary may either or both be metal pipes with their closed lower ends having a threaded portion with a metal cap engaged therewith. The outer housing container may be a sealed aluminum cylinder, and the main inlet and outlet ports of the outer housing container may be the only paths of fluid communication into and out of the autoclave waste fluid disposal device respectively.

During a current sanitization cycle, the outer housing container may be at least partially filled with liquid water resulting from cooling and condensing waste fluid during a previous sanitization cycle. This liquid water helps to absorb heat from hot waste fluid in the coil tube. The liquid water in the outer housing container may rise until reaching the level of the main outlet port and then exit the autoclave waste fluid disposal device through the main outlet port.

BRIEF DESCRIPTION OF THE DRAWINGS

These and other features of the invention are described in further detail in the following description and will be better understood with reference to the accompanying drawings, which are briefly described below.

DETAILED DESCRIPTION

Exemplary embodiments of the invention are described in detail below with reference to the appended figures, wherein like elements are referenced with like numerals throughout. The figures are not necessarily drawn to scale and do not necessarily show every detail or structure of the various embodiments of the invention, but rather illustrate exemplary embodiments and mechanical features in order to provide an enabling description of such embodiments.

An autoclave waste fluid disposal device of the present invention includes an outer housing container with a closed lower end, a main inlet port for receiving waste fluids from an autoclave, and a main outlet port. A multi-chambered condenser is mounted inside the outer housing container and includes an inlet tube, an innermost primary chamber having an open lower end and a sealed upper end with an inlet port connected to the inlet tube. The multi-chambered condenser also includes a secondary chamber enveloping the primary chamber and in communication with the open lower end of the primary chamber. The secondary chamber has an upper end sealed about the inlet tube and at least one secondary chamber outlet port. The multi-chambered condenser also includes a tertiary chamber enveloping the secondary chamber. The tertiary chamber has a closed lower end, an upper end sealed about the inlet tube, and at least one tertiary chamber outlet port in communication with the outer housing container. A coil tube encircles the multi-chambered condenser and has a first end connected to the main inlet port of the outer housing container and a second end connected to the inlet tube of the multi-chambered condenser.

Throughout this specification and the appended claims, it is to be understood that "waste fluid" refers to any mixture of steam, vapor, air and liquid entering the autoclave waste fluid disposal device. Further, it is to be understood that as waste fluid passes through the autoclave waste fluid disposal device, some or all of the steam or vapor in the waste fluid may condense such that liquid water may be present in any or all of the chambers or outer housing container. Thus, the term "fluid" should be interpreted broadly and not in a limiting manner so as to exclude gas/vapor/liquid mixtures.

Figure 1:
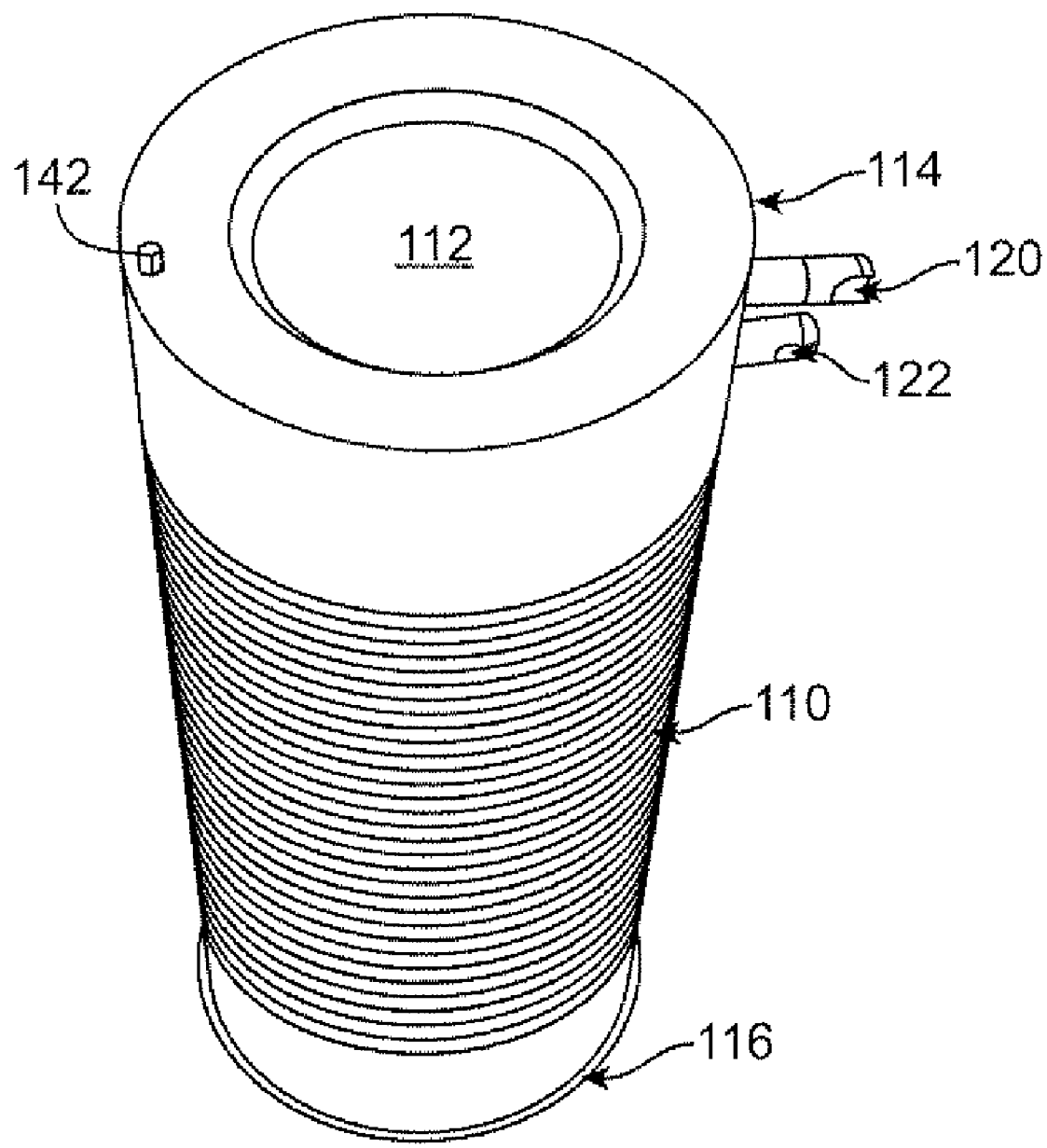
FIG. 1 shows a perspective view of the exterior of an autoclave waste fluid disposal device.

FIG. 1 shows a perspective exterior view of an autoclave waste fluid disposal device 100. Autoclave waste fluid disposal device 100 includes outer housing container 110 having lower end 116 and upper end 114. Cap 112 seals off the interior of outer housing container 110, which in this embodiment is a hollow cylinder. Although outer housing container 110 is a capped hollow cylinder, it is not intended to be pressurized. Adjacent upper end 114 of outer housing container 110 is main inlet port 120 and main outlet port 122. Main inlet port 120 received waste fluid from an autoclave. Main outlet port 122 is the only pathway out of autoclave waste fluid disposal device 100. Therefore, by coupling main outlet port 122 with a drain in communication with a sewer, a user of autoclave waste fluid disposal device 100 can be sure that all waste fluid from the autoclave has been collected and disposed of down the drain. Alternatively, main outlet port 122 may be coupled to a secure container so that waste fluids may be collected for later disposal. Importantly, however, outer housing container 110 is sealed by cap 112 such that it is impossible for any waste fluid to escape from autoclave waste fluid disposal device 100 other than through main outlet port 122. In order to prevent buildup of pressure inside outer housing container 110, pressure relief safety valve 142 may be included. If the pressure inside outer housing container 110 builds above a predetermined safety level, pressure relief safety valve 142 opens to relieve internal pressure. Additionally, a check valve may be incorporated into main outlet port 122 so that no waste fluid "backs up" into autoclave waste fluid disposal device 100 after exiting.

Figure 2:
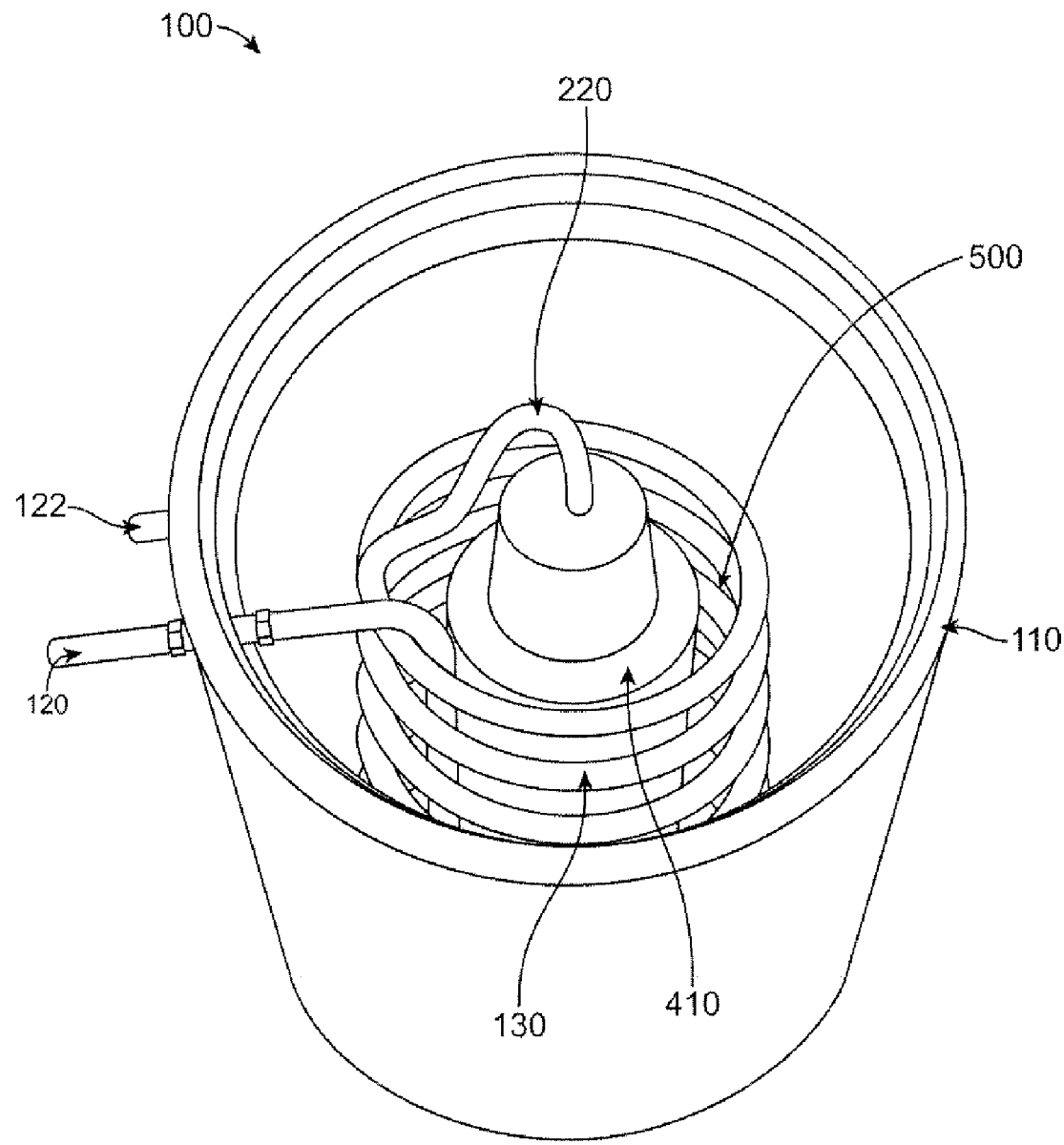
FIG. 2 shows a perspective view of the autoclave waste fluid disposal device of FIG. 1, shown with the cap of the outer housing container removed.

FIG. 2 shows a perspective view of autoclave waste fluid disposal device 100 with cap 112 removed. Coil tube 130 can be seen inside outer housing container 110 and encircling multi-chambered condenser 500. Coil tube 130 provides a path of fluid communication for waste fluid from main inlet port 120 to inlet tube 220 of multi-chambered condenser 500. Although the other chambers of multi-chambered condenser 500 are concealed in this view, the outside surface of tertiary chamber 410 can be seen inside outer housing container 110 and encircled by coil tube 130.

Figure 3:
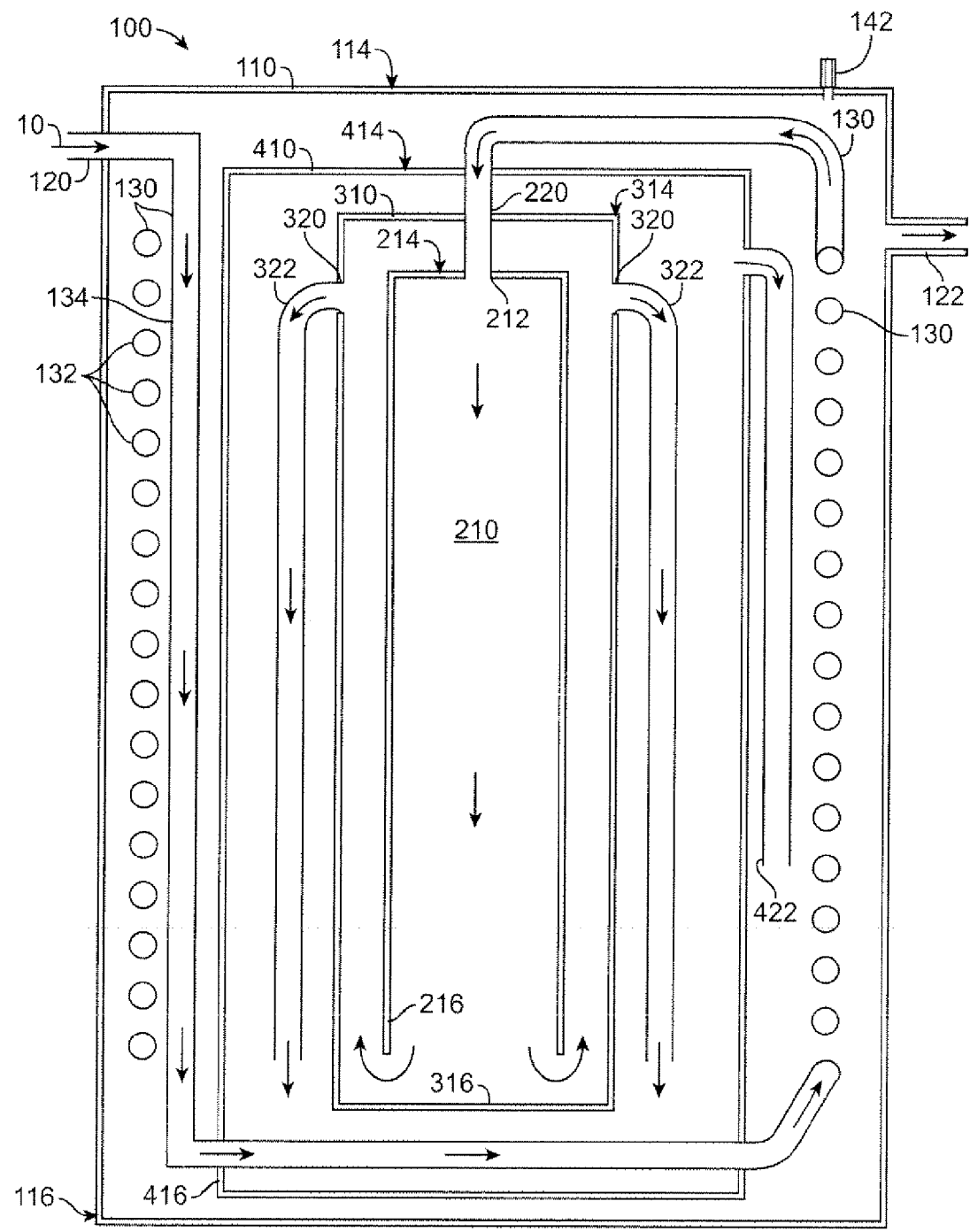
FIG. 3 shows a schematic view of the autoclave waste fluid disposal device of FIG. 1, with arrows indicating the direction of flow.

FIG. 3 shows a schematic view of autoclave waste fluid disposal device 100. Waste fluid 10 emitted from an autoclave enters main inlet port 120 of outer housing container 110. Main inlet port 120 is preferably situated adjacent upper end 114 of outer housing container 110, for example within six inches of upper end 114. Waste fluid 10 then enters coil tube 130, which preferably includes a substantially straight and vertical segment 134 and a plurality of coils 132. The purpose of coils 132 in coil tube 130 is to increase the distance traveled by waste fluid 10 in order to provide more time and surface area for heat transfer. Preferably, but not necessarily, outer housing 110 is at least partially full of liquid water such that coil tube 130 is at least partially submerged, thereby facilitating increased heat transfer and faster cooling of waste fluid 10. Eventually waste fluid 10 reaches the downstream end of coil tube 130, which is connected to inlet tube 220 of multi-chambered condenser 500. Waste fluid 10 passes through inlet tube 220 past primary chamber inlet port 212 into primary chamber 210. Primary chamber 210 is the innermost chamber of multi-chambered condenser 500. Thus, waste fluid 10 enters multi-chambered condenser 500 at its core rather than its outer tertiary chamber 410.

After entering primary chamber 210, waste fluid 10 continues to expand and cool. Lower end 216 of primary chamber 210 is open (i.e. not capped) and is adjacent to (but preferably not contacting) lower end 316 of secondary chamber 310. At this point some portion of waste fluid 10 may have begun to condense such that there is liquid water collected at lower end of secondary chamber 310. However, this is not a requirement and waste fluid 10 may also still be entirely steam or vapor. Waste fluid 10 rises upward in secondary chamber 210, cooling along the way. Eventually waste fluid 10 rises to the level of secondary chamber outlet port 320. Waste fluid 10 then exits secondary chamber 310 and travels down one or more drip tubes 322.

Waste fluid 10 exits drip tubes 322 and enters tertiary chamber 410 adjacent its lower end 416. At this point some portion of waste fluid 10 will likely have begun to condense such that there is liquid water collected at lower end of tertiary chamber 410. However, this is not a requirement and waste fluid 10 may also still be entirely steam or vapor. Waste fluid 10 continues to cool and rise in level until it reaches the level of tertiary chamber outlet port 422. One or more drip tubes is optionally connected to tertiary chamber outlet port(s) 422. Waste fluid 10 exits tertiary chamber outlet port 422 and fills outer housing container. At this point most of the steam in waste fluid 10 has condensed into liquid water, such that outer housing container 110 is at least partially full of water. The presence of this liquid water will improve heat transfer performance when additional cycles are initiated in the future.

Waste fluid 10 in outer housing container 110, which at this point is mostly liquid water, eventually rises to the level of main outlet port 122 where it exits outer housing container 110. Main outlet port 122 may be directly coupled via a pipe to a drain in communication with the local sewer system. Due to the extensive cooling that took place inside autoclave waste fluid disposal device 100, waste fluid 10 is relatively cool so that there is no danger of hot steam entering the drain and causing water in the trap in the drain to boil.

The precise shape and dimensions of autoclave waste fluid disposal device 100 is not critical. However, one of the advantages of the design features of autoclave waste fluid disposal device 100, including multi-chambered condenser 500 and coil tube 130, is that the entire device may be very compact. For example, outer housing container 110 may be a cylinder approximately twelve inches tall and five inches in diameter, with an approximately one-quarter inch thick wall. Primary chamber 210 may be a one-half inch diameter pipe approximately six inches in length. Secondary chamber 310 may be a one inch diameter pipe with a threaded lower end for engagement with a cap to seal off secondary chamber 310. Tertiary chamber 410 may be a three inch diameter pipe with a threaded lower end for engagement with a cap to seal off tertiary chamber 410. Similarly, upper end 414 of tertiary chamber 410 may itself be a threaded cap for engagement with a threaded pipe with a closed lower end.

It can thus be seen that, in one embodiment, multi-chambered condenser 500 is essentially a series of three concentric pipes. Inlet tube 220 leads directly into primary chamber 210 such that waste fluid 10 enters the core of multi-chambered condenser 500 first. Secondary chamber 310 envelopes primary chamber 210. Upper end 314 of secondary chamber 310 is penetrated by and sealed about inlet tube 220. Likewise, tertiary chamber 410 envelopes secondary chamber 310. Upper end 414 of tertiary chamber 410 is also penetrated by and sealed about inlet tube 220.

Autoclave waste fluid disposal device 100 may be made from a wide variety of materials and the precise choice of materials is not critical to the invention. However, the performance of autoclave waste fluid disposal device 100 is improved when the materials used for outer housing container 10, multi-chambered condenser 500, and coil tube 130 have high thermal conductivities. For example, outer housing container 110 is preferably aluminum, while each chamber in multi-chambered housing 500 and coil tube 110 are preferably all copper. Any or all of these materials may be altered to increase the rate of heat transfer. For example, outer housing container 110 may include grooves or striations in order to increase its effective surface area. Although aluminum and copper are disclosed here as acceptable materials for use in building autoclave waste fluid disposal device 100, many other metals and highly thermally conductive materials are also within the scope of the present invention.

Finally, autoclave waste fluid disposal device 100 may be incorporated into an autoclave. For example, the waste fluid exit port of an autoclave may be directly coupled to main inlet port 120 of outer housing container 110. Additionally, autoclave waste fluid disposal device 100 may be used with any type of autoclave that emits a waste fluid. For example, one autoclave with which waste fluid disposal device 100 may be used is the STATIM line of autoclaves, manufactured by SciCan, Ltd. (Toronto, Ontario, Canada).

Various modifications and alterations of the invention will become apparent to those skilled in the art without departing from the spirit and scope of the invention, which is defined by the accompanying claims. Any element in a claim that does not explicitly state "means for" performing a specified function is not to be interpreted as a "means" clause as specified in 35 U.S.C. §112, ¶ 6. The accompanying claims should be constructed with these principles in mind.

What is claimed is:

1. An autoclave waste fluid disposal device, comprising:
    an outer housing container having a closed lower end, a main inlet port for receiving waste fluids from an autoclave, and a main outlet port;
    a multi-chambered condenser mounted inside the outer housing container, the multi-chambered condenser comprising:
        an inlet tube;
        an innermost primary chamber having an open lower end and a sealed upper end with a inlet port connected to the inlet tube;
        a secondary chamber enveloping the primary chamber and in communication with the open lower end of the primary chamber, the secondary chamber having an upper end sealed about the inlet tube and at least one secondary chamber outlet port; and
        a tertiary chamber enveloping the secondary chamber, the tertiary chamber having a closed lower end, an upper end sealed about the inlet tube, and at least one tertiary chamber outlet port in communication with the outer housing container; and
    a coil tube encircling the multi-chambered condenser, the coil tube having a first end connected to the main inlet port of the outer housing container and a second end connected to the inlet tube of the multi-chambered condenser.

2. The autoclave waste fluid disposal device of claim 1, further comprising a drip tube connected to the at least one secondary chamber outlet port and extending toward the lower end of the tertiary chamber.

3. The autoclave waste fluid disposal device of claim 2, further comprising a second secondary chamber outlet port and a second drip tube connected to the second secondary chamber outlet port and extending toward the lower end of the tertiary chamber.

4. The autoclave waste fluid disposal device of claim 1, wherein the main inlet port is adjacent the upper end of the outer housing container, and wherein the coil tube comprises:
   a first segment connected to the main inlet port and extending to the lower end of the outer housing container;
   a second segment extending from the lower end of the outer housing container to the upper end of the multi-chambered condenser, the second segment comprising a plurality of coils encircling the multi-chambered condenser.

5. The autoclave waste fluid disposal device of claim 1, wherein waste fluid from an autoclave enters the main inlet port of the outer housing container, travels through the coil tube into the inlet tube of the multi-chambered condenser and passes through the inlet port of the primary chamber, expands in the primary chamber and travels out the open lower end of the primary chamber into the lower end of the secondary chamber, then rises inside the secondary chamber and exits the secondary chamber outlet port into the tertiary chamber, then exits the tertiary chamber into the outer housing container, then exits the autoclave waste fluid disposal device through the main outlet port of the outer housing container, wherein the waste fluid was condensed and cooled in the autoclave waste fluid disposal device such that liquid water exits the autoclave waste fluid disposal device.

6. The autoclave waste fluid disposal device of claim 1, wherein the main outlet port of the outer housing container is connected to an exit pipe directly connected to a drain pipe in communication with a sewer system.

7. The autoclave waste fluid disposal device of claim 1, wherein the outer housing container is aluminum.

8. The autoclave waste fluid disposal device of claim 1, wherein at least one of the primary chamber, the secondary chamber, and the tertiary chamber is copper.

9. The autoclave waste fluid disposal device of claim 1, wherein the secondary chamber is a metal pipe and the closed lower end of the secondary chamber comprises a first threaded portion with a first metal cap engaged therewith.

10. The autoclave waste fluid disposal device of claim 9, wherein the tertiary chamber is a metal pipe and the closed lower end of the tertiary chamber comprises a second threaded portion with a second metal cap engaged therewith.

11. The autoclave waste fluid disposal device of claim 10, wherein the outer housing container is a sealed aluminum cylinder.

12. The autoclave waste fluid disposal device of claim 11, wherein the main inlet and outlet ports of the outer housing container are the only paths of fluid communication into and out of the autoclave waste fluid disposal device respectively.

13. The autoclave waste fluid disposal device of claim 1, wherein during a current cycle the outer housing container is at least partially filled with liquid water resulting from cooling and condensing waste fluid during a previous cycle, the liquid water absorbing heat from waste fluid in the coil tube.

14. The autoclave waste fluid disposal device of claim 13, wherein the liquid water in the outer housing container rises until reaching the level of the main outlet port and then exits the autoclave waste fluid disposal device through the main outlet port.

15. A medical equipment sanitization device, comprising;
   an autoclave having a waste fluid exit port;
   an outer housing container having a closed lower end, a main inlet port coupled to the waste fluid exit port of the autoclave, and a main outlet port;
   a multi-chambered condenser mounted inside the outer housing container, the multi-chambered condenser comprising:
      an inlet tube;
      an innermost primary chamber having an open lower end and a sealed upper end with a inlet port connected to the inlet tube;
      a secondary chamber enveloping the primary chamber and in communication with the open lower end of the primary chamber, the secondary chamber having an upper end sealed about the inlet tube and at least one secondary chamber outlet port; and
      a tertiary chamber enveloping the secondary chamber the tertiary chamber having a closed lower end an upper end sealed about the inlet tube, and at least one tertiary chamber outlet port in communication with the outer housing container; and
   a coil tube encircling the multi-chambered condenser, the coil tube having a first end connected to the main inlet port of the outer housing container and a second end connected to the inlet tube of the multi-chambered condenser.

16. The medical equipment sanitization device of claim 15, further comprising a drip tube connected to the at least one secondary chamber outlet port and extending toward the lower end of the tertiary chamber.

17. The medical equipment sanitization device of claim 16, further comprising a second secondary chamber outlet port and a second drip tube connected to the second secondary chamber outlet port and extending toward the lower end of the tertiary chamber.

18. The medical equipment sanitization device of claim 15, wherein the main inlet port is adjacent the upper end of the outer housing container, and wherein the coil tube comprises:
   a first segment connected to the main inlet port and extending to the lower end of the outer housing container;
   a second segment extending from the lower end of the outer housing container to the upper end of the multi-chambered condenser, the second segment comprising a plurality of coils encircling the multi-chambered condenser.

* * * * *